UNITED STATES PATENT [19] [11] 4,422,447
Schiff [45] Dec. 27, 1983

[54] PERCUTANEOUS BALLOON
[76] Inventor: Peter Schiff, Rte. 7, Cookeville, Tenn. 38501
[21] Appl. No.: 253,680
[22] Filed: Apr. 13, 1981
[51] Int. Cl.³ ................... A61B 19/00; A61M 25/00
[52] U.S. Cl. ................................. 128/1 D; 128/344; 604/162
[58] Field of Search ............ 128/657, 772, 348–350 R, 128/344, 325, 1 D, DIG. 9; 604/162

[56] References Cited
U.S. PATENT DOCUMENTS

| | | | |
|---|---|---|---|
| 3,438,373 | 4/1969 | Pannier | 128/214.4 |
| 3,757,771 | 9/1973 | Ruegg et al. | 128/214.4 |
| 4,096,860 | 6/1978 | McLaughlin | 128/214.4 |
| 4,122,858 | 10/1978 | Schiff | 128/348 |
| 4,261,339 | 4/1981 | Hanson et al. | 128/1 D |
| 4,276,874 | 7/1981 | Wolvek et al. | 128/1 D |
| 4,292,974 | 10/1981 | Fogarty et al. | 128/344 |
| 4,362,150 | 12/1982 | Lombardi et al. | 128/1 D |

FOREIGN PATENT DOCUMENTS

| | | | |
|---|---|---|---|
| 156901 | 9/1956 | Sweden | 128/348 |
| 2037166 | 7/1980 | United Kingdom . | |

Primary Examiner—Dalton L. Truluck
Attorney, Agent, or Firm—Weinstein & Sutton

[57] ABSTRACT

An intra-aortic balloon designed for percutaneous insertion. An inflatable intra-aortic balloon of reduced diameter, when inflated, has its proximal end secured to a catheter. A stylet extends through said balloon and is anchored in a tip provided at the distal end of the balloon. The stylet extends from said tip through said balloon and through at least a portion of said catheter. A balloon coupling comprised of a "Y" member is provided with a linear bore communicating with said catheter and a branch bore intersecting with said linear through bore. The stylet extends partially into said through bore and said branch bore and has its proximal end coupled to a control knob assembly threadedly engaged with the rear end of said branch-bore and movable when rotated in a first direction to simultaneously twist and elongate the intra-aortic balloon and when rotated in the reverse direction to simultaneously untwist and relieve the elongated condition. The twisting of the control knob, twists the stylet and the tip, causing the balloon to be twisted as it is being lengthened. The lengthening of the balloon prevents the balloon membrane from "doubling up" as it is twisted. The twisting operation significantly reduces the exterior balloon diameter enabling the balloon to fit through a small diameter percutaneous sheath inserted into an artery. The screw threads on the balloon luer are precisely designed to limit the maximum travel preventing an operator from turning the stylet beyond the "wrapped for insertion" position and also preventing the stylet from moving beyond the totally unwrapped position after the balloon is properly placed in the patient. A catheter adapter slidably mounted on the catheter is inserted into a sheath collar which retains the adapter within the collar and provides a blood-tight seal preventing blood from exiting from the sheath.

2 Claims, 9 Drawing Figures

4,422,447

PERCUTANEOUS BALLOON

FIELD OF THE INVENTION

The present invention relates to intra-aortic balloons and more particularly to novel apparatus for adapting an intra-aortic balloon for percutaneous insertion by means which simultaneously elongates and twists the intra-aortic balloon for insertion and simultaneously untwists and eases the aforesaid elongation in readiness for use of the balloon in the operative position.

BACKGROUND OF THE INVENTION

Intra-aortic balloons are well known in the art as medical appliances capable of providing assistive pumping for a weak heart. Conventional intra-aortic balloons have been described for example in U.S. Pat. No. 4,016,871 issued Apr. 12, 1977 to the present inventor. Traditionally, intra-aortic balloons, as well as other catheters, were both inserted into a patient and removed therefrom through the use of a surgical procedure. The tedious surgical technique led to the development and adoption of the Seldinger Catheterization Technique which is now a well known and well established procedure in daily use since at least 1976 and involves a percutaneous invasion of the arterial system without resorting to a surgical procedure.

The availability of the Seldinger Technique led to the development of an intra-aortic balloon described in the British Publish Patent Application No. GB Pat. No. 2,037,166 published July 9, 1980 in which a technique is described wherein an intra-aortic balloon is manually twisted to reduce its outer diameter, a vacuum is drawn to retain the intra-aortic balloon in the twisted, reduced diameter state. The twisted intra-aortic balloon is then inserted into the patient percutaneously, employing the Seldinger Technique. After insertion, the vacuum condition is removed to permit use of the balloon.

The above-mentioned design has led to a number of disadvantages in that no specific technique is available for insuring that the intra-aortic balloon has been completely untwisted once it is moved to the operative position. In addition, the need for manual twisting of the balloon complicates the insertion procedure and increases the time required to perform the procedure. Also there is no means for positively assuring that the balloon will be untwisted after insertion. Through the use of the novel technique and apparatus of the present invention, it is possible to eliminate the step of drawing a vacuum in the balloon as is required in the prior art techniques.

BRIEF DESCRIPTION OF THE INVENTION

The present invention is characterized by comprising a novel intra-aortic balloon designed for percutaneous insertion and which eliminates the disadvantages of the aforementioned prior art percutaneous balloons.

The present invention is characterized by comprising an intra-aortic balloon terminating in a tip arranged at its distal end and being joined with a catheter at its proximal end. A slender stylet is anchored within the aforesaid tip and extends rearwardly through said intra-aortic balloon and into said catheter. A holder is arranged a spaced distance inwardly from the point of connection between said catheter and the proximal end of said balloon and is provided with a substantially linear through bore which communicates with said catheter and a branch bore having a forward end communicating with the through bore and a rearward end which is tapped for threaded engagement with a threaded member secured at one end to an adjustment knob. The aforementioned stylet extends partially into the forward end of the through-bore and into the branch bore of said stylet receiving holder and has its proximal end anchored to the aforementioned threaded portion of said control knob. Positive and negative pulsatile pressure for respectively inflating and deflating said intra-aortic balloon, communicates with said balloon through said through-bore and said catheter. The stylet is sufficiently slender relative to the inner diameter of the catheter and the balloon to avoid impeding the inflation and deflation operation of the intra-aortic balloon.

In order to prepare the balloon for insertion, the aforementioned control knob is twisted, simultaneously causing the stylet, the tip and the balloon to undergo twisting. The direction of twisting of the control knob and its threaded portion also linearly moves the distal end of said stylet away from the proximal end of said balloon causing an elongation thereof. Thus the balloon simultaneously undergoes twisting and elongation. The twisting action significantly reduces the outer diameter of the balloon, making it extremely advantageous for percutaneous insertion through a small diameter sheath of a percutaneous insertion set. The simultaneous elongation of the balloon prevents the twists formed in the balloon material from "doubling up" so as to retain the aforesaid reduced low profile outer diameter of the balloon.

The balloon is then inserted percutaneously. After insertion is completed, the aforementioned control knob is twisted in the reverse direction causing its threaded member, the stylet, the tip and the balloon to untwist. At the same time; the stylet and tip move rearwardly toward the proximal end of the balloon thus easing the aforementioned elongation condition. The number of turns which the knob is capable of undergoing is precise, thus assuring that the balloon will be completely untwisted and will not be twisted in the reverse direction. The integrity of both the twisting and untwisting operation is assured through the use of an extremely rugged reliable and yet slender stylet, preferably formed of a resilient and yet extremely durable stainless steel wire which, under life testing has shown to be capable of having an extremely long, useful operating life, well beyond the life of the intra-aortic balloon itself.

The percutaneous sheath is provided with a collar which receives a catheter adapter slidably mounted on the balloon catheter. The adapter is retained within the interior of the sheath collar and provides a blood-tight seal which prevents blood from escaping from the percutaneous sheath.

OBJECTS OF THE INVENTION AND BRIEF DESCRIPTION OF THE FIGURES

It is therefore one object of the present invention to provide a novel intra-aortic balloon designed for percutaneous insertion and including means for positively wrapping and unwrapping the intra-aortic balloon.

Still another object of the present invention is to provide a novel intra-aortic balloon including means for positively and simultaneously twisting and elongating said balloon to provide a significantly reduced outer diameter which is extremely advantageous fo percutaneous insertion, said elongation preventing the twists in said balloon from "doubling up" and thereby increasing the outer diameter.

Still another object of the present invention is to provide an intra-aortic balloon advantageously adapted for percutaneous insertion and employing a stylet and means for rotating and linearly moving said stylet in first and second opposing directions to respectively provide the balloon with a significantly reduced outer diameter advantageous for percutaneous insertion and for positively untwisting said balloon to be assured of its proper and optimum operation after insertion.

Still another object of the invention is to provide a balloon for percutaneous insertion and having a catheter adapter which cooperates with a percutaneous sheath to provide a blood-tight seal and lock the adapter in the sealing position.

The above as well as other objects of the present invention will become apparent when reading the accompanying description and drawing, in which:

FIG. 1 shows a percutaneous balloon structure embodying the principles of the present invention.

FIGS. 1a and 1b respectively show perspective views of an inflated balloon and a twisted balloon ready for percutaneous insertion.

DETAILED DESCRIPTION OF THE INVENTION

Figures 1, 1A, 1B:
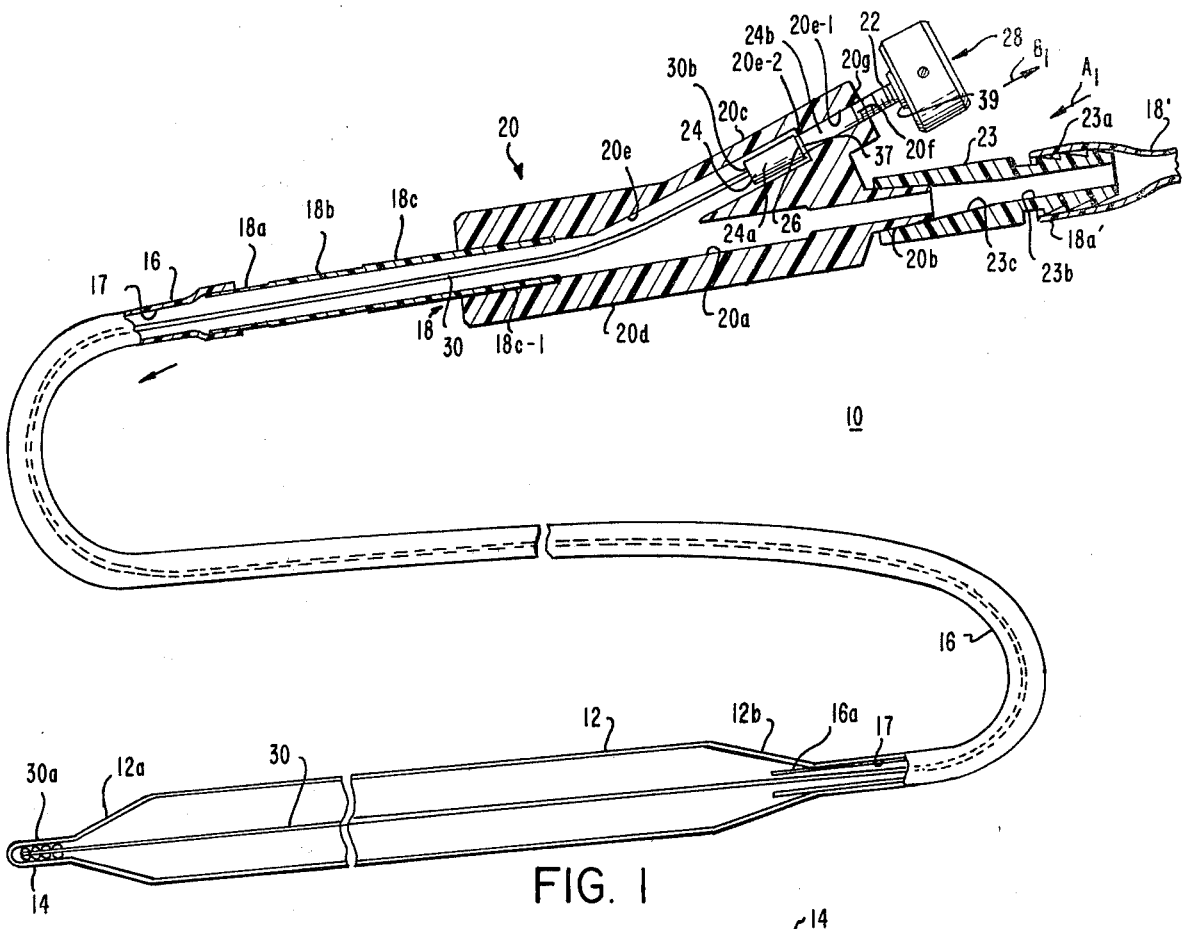

FIG. 1 shows an intra-aortic balloon assembly 10 embodying the principles of the present invention and comprised of an intra-aortic balloon 12 formed of a pliable thin gauge plastic material which is capable of stretching to only a minor degree to provide a controlled maximum diameter when fully inflated. The forward end 12a of balloon 12 is tapered as shown and terminates in a tip 14 at its distal end as shown. The rearward end of balloon 12 is similarly tapered at 12b and is thereafter of a constant diameter and defines the forward end 16a of a catheter outer shell 16. The catheter outer shell 16 and balloon 12 in the preferred embodiment, is formed of one continuous outer shell, preferably of polyurethane, and without seams. The outer shell portion 16 of the continuous sheath is provided with a thin, hollow inner shell 17, preferably formed of thin gauge polyethylene. The inner and outer shells extend rearwardly to the balloon coupling 20. The rearward ends 16b and 17b of catheter shells 16 and 17 are force fittingly mounted upon the left-hand end 18a of the stepped connector 18 having outer diameter portions 18a, 18b and 18c of increasingly larger diameters. End 18c-1 of portion 18c is force-fittingly inserted into the left-hand end of a through bore 20a provided in balloon coupling 20 which is a substantially rigid member preferably formed of a suitable plastic material and having a substantially linear through bore 20a extending from its left-hand end through the main body 20d thereof and through a tapered rearwardly extending projection 20b. Second catheter 18' has its left-hand end 18a' force fittingly mounted upon a female extension luer 23 having a barbed end 23a and a substantially cylindrical shaped bore 23b extending through the length of the main body portion of luer 23 and barbed projection 23a. The left-hand end of bore 23b is tapered at 23c in order to force fittingly receive the tapered projection 20b for coupling the intra-aortic balloon 12 to a source of pulsatile pressure (not shown) for inflating and deflating balloon 12.

Coupling 20 is further provided with a diagonally aligned section 20c integral with the main body portion 20d and provided with a branch bore 20e communicating with the main through-bore 20a at a location intermediate to the ends of bore 20a, said branch bore extending rearwardly and communicating with an opening 20f in the rear wall 20g of branch section 20c. The rearward section 20e-1 of branch bore 20e is of a reduced diameter. A shoulder 20e-2 is formed at the point where reduced diameter bore 20e-1 meets the larger diameter bore 20e.

A threaded screw 22 threadedly engages tapped bore 20e-1. A substantially cylindrical-shaped solid body 24, integral with screw 22, has an enlarged diameter portion 24a relative to screw 22 and a small diameter portion 24b forming a shoulder 26 at the point where larger diameter portion 24a joins reduced diameter portion 24b. The right-hand end of screw 22 is provided with a manually operable adjustment knob 28 integrally joined to screw 22 for turning screw 22 in the tapped portion 20e-1 of bore 20e.

Resilient washers 37 and 39 may be provided to air tightly seal coupling 20, preventing air from entering or leaving opening 20e when knob 28 is in either of its two extreme end positions.

In one preferred embodiment, balloon coupling 20 is preferably formed of a plastic material such as, for example, nylon. As shown best in FIG. 2a, bore portion 20e-1 and shoulder 20e-2 meet and form a sharp corner at 20e-3. The shoulder 26 between enlarged diameter body portion 24a and reduced diameter portion 24b is preferably tapered. When knob 28 is rotated in the direction causing body portions 24a and 24b to move in the direction of arrow $B_1$, the tapered or diagonally aligned shoulder 26 bears against the sharp corner 20e-3 to assure a firm air and liquid-tight seal therebetween. Knob 28 is provided with a centrally located bore (not shown) and a radially aligned threaded bore intersecting with the aforementioned axially aligned bore. A set screw 19 threadedly engages threaded bore 28a to secure knob 28 to body portion 24b-1 as shown in FIG. 2a.

A slender stylet 30 formed of a bendable and yet durable material such as stainless steel, for example, has its forward end 30a fixedly secured and anchored within balloon tip 14. Stylet 30 extends rearwardly through balloon 12, catheter 16, coupling member 18 and the forward portion of main bore 20a. The stylet 30 thereafter is gently curved and extends into branch bore 20e and has its rearward end 30b anchored to the left-hand end of solid cylindrical member 24. Rearward end 30b of stylet 30 is preferably silver soldered into member 24 so that any turning motion and/or linear motion of member 24 is directly imparted to stylet 30. Similarly as was described above, tip 14 is fixedly secured to the forward end 30a of stylet 30 so that any rotational and/or linear movement experienced by stylet 30, is directly imparted to tip 14.

Figure 3:
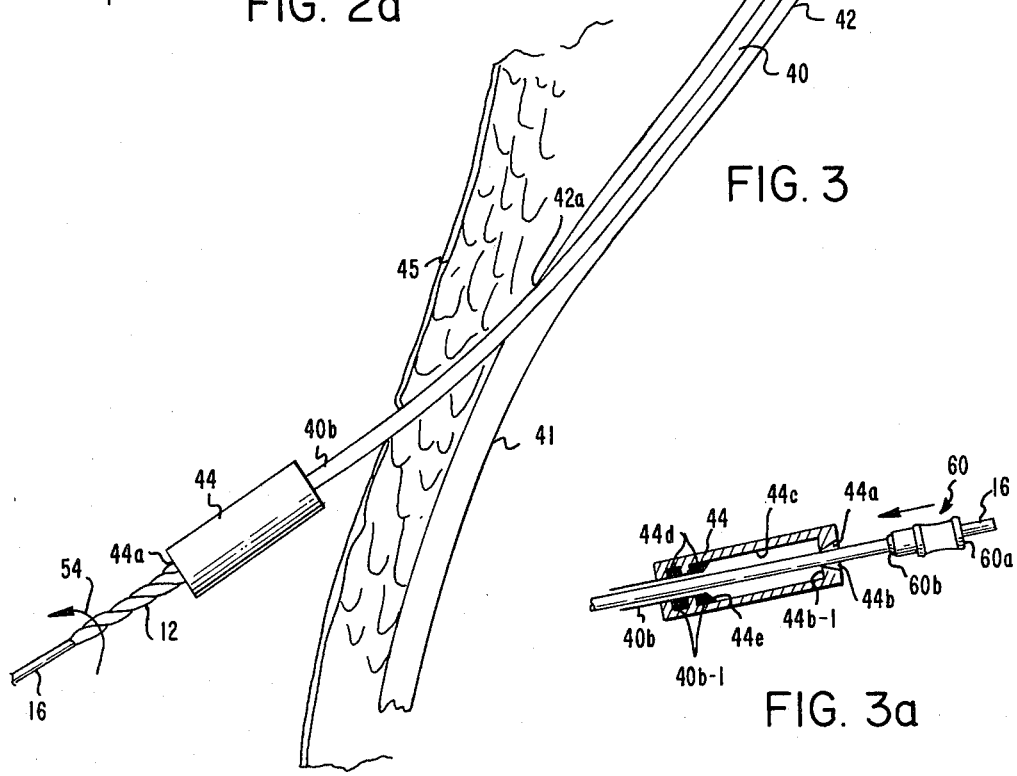
FIG. 3 shows a simplified diagram of the general manner in which a percutaneous insertion is made.

As was described hereinabove, in order to implant intra-aortic balloon 12 through the use of a percutaneous insertion technique and specifically the Seldinger Technique, a hypodermic needle (not shown) is inserted through the skin and, in the case of intra-aortic balloon insertion, the needle perforates the femoral artery 41, shown in FIG. 3. When blood spurts from the open external end of the needle, placement of the hypodermic needle (not shown) within the femoral artery 41 is confirmed. A guide wire is then placed into the artery 42 by passing the guide wire through the center of the hollow needle and into the iliac artery bifurcation. The hypodermic needle is then removed while the wire is maintained in the aforesaid position within the artery. A dilator is placed over the guide wire and advanced through the skin and into the femoral artery in order to dilate (i.e. enlarge) the artery. Subsequently the dilator is removed and a larger dilator/sheath is advanced into the artery over the guide wire. The guide wire is then removed, leaving the dialator/sheath 40 in place and extending through the femoral artery 41, available for insertion of a balloon catheter assembly 10 into the aorta without surgery. FIG. 3 shows the sheath 40 arranged within the iliac artery 42, the forward (distal) end 40a being open. Sheath 40 extends rearwardly and through the puncture 42a formed in the femoral artery 41, by the hypodermic needle as was described hereinabove, and extends outwardly through the skin 45. A coupling 44 is joined to the rearward end 40b of sheath 40 and has an opening 44a for receiving the intra-aortic balloon 12 and a catheter adaptor 60, as will be more fully described.

The balloon insertion operation is as follows:

As one optional approach, the balloon 12 is dipped in a sterile saline solution. As one optional approach, a stopcock 46 (see FIG. 4a), having an opening at its rearward end 46a, is mounted to coupling projection 20b and is placed in the open position. A syringe 48 is inserted into stopcock 46 to empty balloon 12. Thereafter, stopcock 46 is closed and the syringe 48 is removed from the stopcock 46. The closure of stop cock 46 prevents balloon 12 from being refilled with air.

Figure 4A:
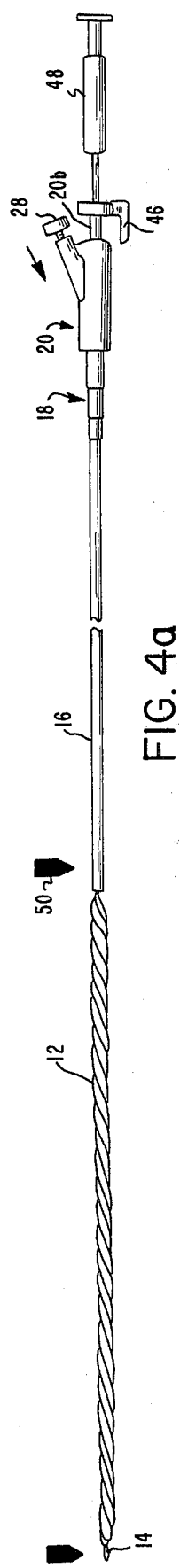
FIGS. 4a and 4b show simplified views of the intra-aortic balloon assembly useful in explaining the steps followed for percutaneous insertion.

As a preferred technique, the syringe and stopcock may be eliminated for purposes of deflating balloon 12. As an alternative, balloon 12 is simply stripped by placing balloon 12 between the fingers and squeezing the balloon while moving the fingers from tip 14 to point 50 as shown in FIG. 4a in order to empty the balloon of air. This technique is preferred over the vacuum drawing technique since it has been found that an excessive vacuum condition creases the balloon membrane and holds the folded layers so tightly that the balloon 12 does not wrap well. The wrapping of the balloon 12 has been found to be more effective and compact when the contents of the balloon 12 are evacuated simply by stripping the balloon between the fingers, as described.

The knob 28 is rotated in the clockwise direction. The balloon 12 is held at location 50 and tip 14 is gently rotated to assist the wind-up, i.e. the twisting of balloon 12. Balloon 12 is then stripped lightly by moving the fingers along balloon 12 from point 50 toward tip 14 to smooth out the balloon 12 and thereby minimize its outer diameter. The elongation of balloon 12 prevents the twists in the balloon 12 from "doubling over". Balloon 12 is hollow except for the presence of stylet 30, enabling the balloon 12 to wrap itself about stylet 30 which serves as the means for supporting the balloon 12 in its elongated state.

Figure 2:
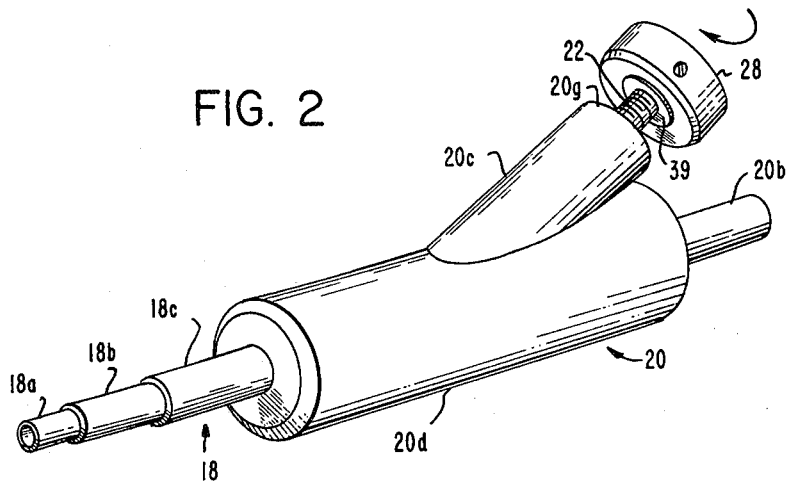
FIG. 2 shows a perspective view of the intra-aortic balloon coupling employed in the assembly of FIG. 1.
Figure 2A:
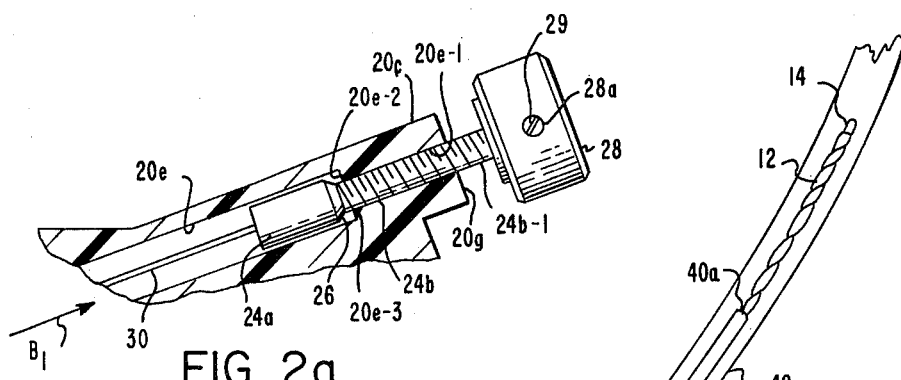
FIG. 2a is an enlarged sectional view of a portion of the balloon coupling of FIG. 2.

As shown in FIG. 2, the above steps are repeated until control knob 28 can no longer be turned in the clockwise direction. This occurs when the left-hand surface of knob 28 engages the rear surface 20g of coupling 20.

Figure 4B:
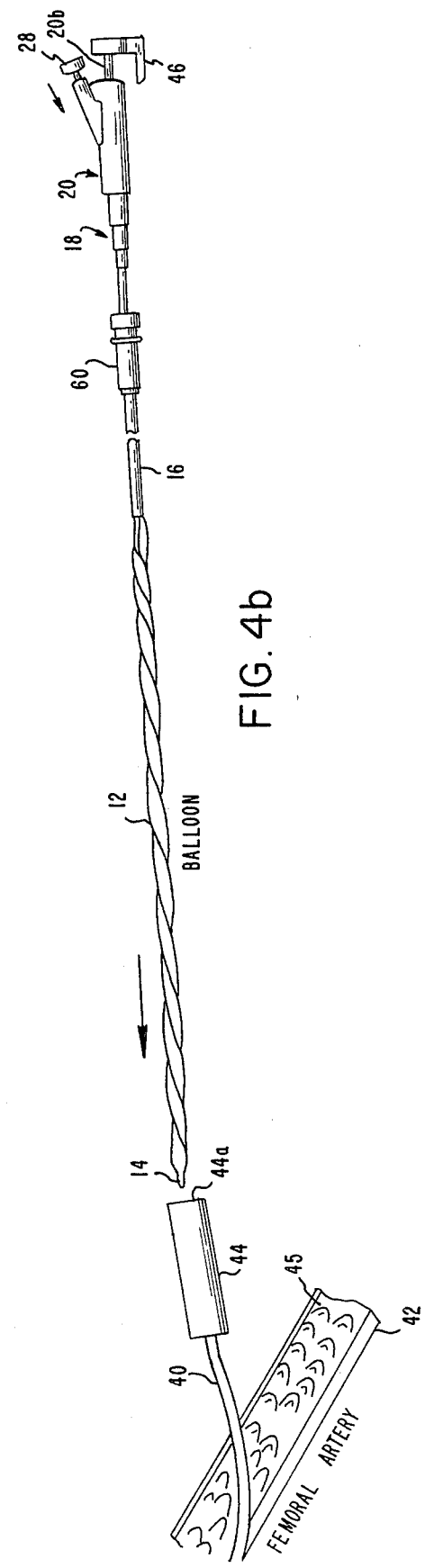

Returning to FIG. 4b, thereafter balloon 12 is again briefly dipped into a sterile saline solution, and tip 14 is inserted into opening 44a of coupling 44 and is pushed through coupling 44 and hollow sheath 40. Balloon 12 may be twisted counter-clockwise during insertion, as shown by arrow 54 in FIG. 3, only as needed during the insertion operation.

When balloon 12 is in the operative position, with tip 14 in the aortic arch, catheter adapter 60, described in detail in U.S. Pat. No. 4,122,858 issued Oct. 31, 1978 to this inventor, is pushed along the catheter 16 of intra-aortic balloon assembly 10 and into the opening 44a in percutaneous sheath collar 44.

Figure 3A:
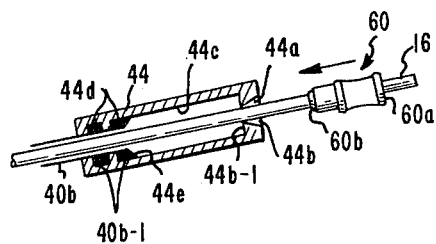
FIG. 3a is an enlarged sectional view of the percutaneous sheath shown in FIG. 3.

As can best be seen from FIG. 3a, the opening 44a in percutaneous sheath collar 44 is provided with a tapered wall 44b which communicates with a hollow interior 44c of larger diameter, forming the shoulder 44b-1. This arrangement enables catheter adapter 60 to slide along catheter 16 and past the tapered wall 44b to enter into the hollow interior 44c. The sheath 44 has some resilience in order to yield outwardly as catheter adapter 60 is pressed into opening 44a. As soon as the rearward surface 60a of catheter adapter 60 clears the tapered side wall 44b, the yielding opening contracts, locking the right-hand surface of catheter adapter 60a by means of interior shoulder 44b-1. The percutaneous sheath 40 has its rearward end 40b extending inwardly into the left-hand end of percutaneous sheath collar 44 and it is anchored within grooves 44d, the right-hand most end 40b-1 conforming to the shape of the recesses 44d provided in collar 44 to secure the right-hand end of sheath 40 to sheath collar 44. The catheter adapter 60, as is described in detail in aforementioned U.S. Pat. No. 4,122,858, provides an air and liquid-tight seal between adapter 60 and catheter 16. The locking means in the form of shoulder 44b-1 and the rear surface 60a of catheter adapter 60 cooperate to prevent catheter adapter 60 from being removed from collar 44. The interior periphery of opening 44c forms a tight fit with the outer periphery of adapter 60 to form a blood-tight seal therebetween, preventing blood which may pass between sheath 40 and catheter 16 from exiting through opening 44a.

Control knob 28 is then rotated counter-clockwise until it can no longer be rotated in this direction. This counter-clockwise rotation untwists balloon 12, completing the insertion operation.

As was mentioned hereinabove, to twist balloon 12, control knob 28 is rotated clockwise causing screw 22 and cylindrical body 24 to also rotate clockwise, imparting clockwise rotation to stylet 30. Stylet 30, in turn rotates tip 14 causing balloon 12 to be twisted about stylet 30.

According to FIG. 1, simultaneously therewith the rotation of screw 22 causes screw 22 to move linearly in the direction shown by arrow A1 causing screw 22, member 24 and stylet 30 to move in the direction shown by arrow A2, thereby causing tip 14 to move away from balloon coupling 20, to simultaneously elongate balloon 12 as it is being twisted, to prevent the twists being formed in balloon 12 from being "doubled over" whereby the twisted balloon 12 presents a significantly reduced outer diameter making the intra-aortic balloon assembly 10 extremely advantageous for use in percutaneous insertion such as through the use of the above described Seldinger Technique.

To remove balloon 12 from the body, the balloon is deflated and similarly re-twisted by means of knob 28 and is then pulled back through sheath 42.

The outer diameter of stylet 30 is extremely slender. In one preferred embodiment the diameter of stylet 30 is 0.026 inches, thus, stylet 30 does not interfere with positive and negative pulsatile pressure pulses passing through coupling 20, catheter 16 and balloon 12 during the operation of intra-aortic balloon 12. A type No. 302 stainless steel wire which has been utilized for stylet 30 provides excellent performance over long periods of time without failure. However, although stainless steel stylets are preferred, any other material exhibiting similar operating characteristics, may be employed if desired.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An intra-aortic balloon assembly comprising:
an elongated intra-aortic balloon means having a distal end and a proximal end;
said distal end terminating in a tip;
coupling means being joined to said proximal end for introducing pulsatile pressure through said coupling means to said balloon means for selective inflation and deflation of said balloon means;
elongated catheter means extending between said coupling means and said intra-aortic balloon means;
catheter adapter means slidably mounted on said catheter means for providing a slidable liquid-tight seal between said catheter adapter means and said catheter means;
an elongated percutaneous sheath having a first end for insertion into a vessel and having a second end for receiving an intra-aortic balloon;
a percutaneous sheath collar secured to said second end;
said percutaneous sheath collar having a hollow interior, a first end of said percutaneous sheath collar being joined to said percutaneous sheath and a second end thereof being provided with resilient locking means;
said catheter adapter means being slidable through said second end past said locking means and into the hollow interior of said percutaneous sheath collar whereby said adapter means is fully enclosed by said percutaneous sheath collar and said locking means retains said catheter adapter means within said percutaneous sheath collar and whereby said percutaneous sheath collar and said catheter adapter means cooperate to provide a second liquid-tight seal between said sheath and said adapter means.

2. The assembly of claim 1 wherein said coupling means includes means for selectively twisting and untwisting said intra-aortic balloon means and having a manually operable member for twisting said balloon means when said manually operable member is moved in a first direction and for untwisting said balloon means when said manually operable means is moved in a second direction.

* * * * *

UNITED STATES PATENT AND TRADEMARK OFFICE
CERTIFICATE OF CORRECTION

PATENT NO. : 4,422,447
DATED : December 27, 1983
INVENTOR(S) : Schiff

It is certified that error appears in the above—identified patent and that said Letters Patent is hereby corrected as shown below:

In the Abstract:

Second column, line 21, change "sheat" to --sheath--.

Column 1:

Line 30, delete "Pat. No."

Column 4:

Line 50, change "19" to --29--.

Signed and Sealed this

Twenty-second Day of October 1985

[SEAL]

Attest:

DONALD J. QUIGG

Attesting Officer

Commissioner of Patents and Trademarks—Designate